(12) United States Patent
Walters et al.

(10) Patent No.: US 8,848,194 B2
(45) Date of Patent: Sep. 30, 2014

(54) INTEGRATED PLASMONIC NANOCAVITY SENSING DEVICE

(75) Inventors: Robert Walters, Redwood City, CA (US); Jurriaan Schmitz, Hengelo (NL); Albert Polman, Amsterdam (NL); Ihor Brunets, Steinfurt (DE)

(73) Assignee: Integrated Plasmonics Corporation, San Francisco, CA (US)

( * ) Notice: Subject to any disclaimer, the term of this patent is extended or adjusted under 35 U.S.C. 154(b) by 32 days.

(21) Appl. No.: 13/639,716

(22) PCT Filed: Apr. 6, 2011

(86) PCT No.: PCT/EP2011/055322
§ 371 (c)(1),
(2), (4) Date: Feb. 19, 2013

(87) PCT Pub. No.: WO2011/124593
PCT Pub. Date: Oct. 13, 2011

(65) Prior Publication Data
US 2013/0148126 A1    Jun. 13, 2013

Related U.S. Application Data

(60) Provisional application No. 61/420,014, filed on Dec. 6, 2010.

(30) Foreign Application Priority Data

Apr. 6, 2010   (EP) ..................................... 10159175

(51) Int. Cl.
| | |
|---|---|
| *G01N 21/55* | (2014.01) |
| *G01N 21/64* | (2006.01) |
| *H01L 31/12* | (2006.01) |
| *B82Y 20/00* | (2011.01) |
| *G02B 6/122* | (2006.01) |
| *G01N 21/77* | (2006.01) |
| *B01L 3/00* | (2006.01) |

(52) U.S. Cl.
CPC ......... *G01N 21/55* (2013.01); *B01L 2300/0663* (2013.01); *G01N 21/648* (2013.01); *G01N 21/554* (2013.01); *H01L 31/125* (2013.01); *B01L 2300/0654* (2013.01); *G01N 2021/7789* (2013.01); *G01N 21/7746* (2013.01); *G01N 2021/7776* (2013.01); *B01L 3/502715* (2013.01); *G01N 2021/7786* (2013.01); *G01N 21/6489* (2013.01); *B82Y 20/00* (2013.01); *G02B 6/1226* (2013.01); *G01N 21/6454* (2013.01)
USPC ........................................................ 356/445

(58) Field of Classification Search
CPC ..... G01N 21/553; G01N 21/55; B82Y 20/00; B82Y 30/00; B82Y 40/00; B82Y 10/00; B82Y 15/00; B82Y 35/00; B02B 6/1226; G02B 6/1226; G02B 5/008; G02B 6/107; G02B 6/12004; G02B 6/12007; G02B 6/1225; G02B 6/34; G02B 5/288; G02B 2006/1206
See application file for complete search history.

(56) References Cited

U.S. PATENT DOCUMENTS

| 6,078,705 A | 6/2000 | Neuschafer et al. |
| 6,410,115 B1 | 6/2002 | Tsai et al. |

(Continued)

FOREIGN PATENT DOCUMENTS

WO    2009/112288 A1    9/2009

OTHER PUBLICATIONS

Adams et al., "Microfluidic integration on detector arrays for absorption and fluorescence micro-spectrometers," Sensors and Actuators A 104:25-31, 2003.

(Continued)

*Primary Examiner* — Michael P Stafira
(74) *Attorney, Agent, or Firm* — Seed IP Law Group PLLC

(57) ABSTRACT

An integrated plasmonic sensing device is described wherein the integrated device comprises: at least one optical source comprising a first conductive layer and a second conductive layer, and a optical active layer between at least part of said first and second conductive layers; at least one nanocavity extending through said first and second conductive layers and said optical active layer, wherein said optical source is configured to generate surface plasmon modes suitable for optically activating one or more resonances in said nanocavity; and, at least one optical detector comprising at least one detection region formed in said substrate in the vicinity of said nanocavity resonator, wherein said optical detector is configured to sense optically activated resonances in said nanocavity.

16 Claims, 7 Drawing Sheets

(56) References Cited

U.S. PATENT DOCUMENTS

| | | | |
|---|---|---|---|
| 6,437,345 | B1 | 8/2002 | Bruno-Raimondi et al. |
| 6,448,064 | B1 | 9/2002 | Vo-Dinh et al. |
| 6,469,785 | B1 | 10/2002 | Duveneck et al. |
| 7,483,140 | B1 | 1/2009 | Cho et al. |
| 7,768,650 | B2 | 8/2010 | Bazylenko |
| 7,773,228 | B1 | 8/2010 | Hollingsworth et al. |
| 2006/0197960 | A1* | 9/2006 | Bazylenko .............. 356/491 |
| 2007/0052049 | A1 | 3/2007 | Bahl et al. |
| 2008/0198376 | A1 | 8/2008 | Poponin |
| 2008/0280374 | A1 | 11/2008 | Potyrailo et al. |
| 2009/0027681 | A1* | 1/2009 | De Vlaminck et al. ....... 356/445 |
| 2009/0273779 | A1 | 11/2009 | Baumberg et al. |
| 2010/0320444 | A1 | 12/2010 | Dutta |
| 2011/0037981 | A1 | 2/2011 | Zhu et al. |
| 2011/0079869 | A1 | 4/2011 | Mazzillo |
| 2011/0109902 | A1 | 5/2011 | Lin et al. |
| 2012/0205767 | A1* | 8/2012 | Bai et al. .................. 257/432 |

OTHER PUBLICATIONS

Dionne et al., "Plasmon slot waveguides: Towards chip-scale propagation with subwavelength-scale localization," Physical Review B 73:035407, 2006, 9 pages.

Ebbesen et al., "Extraordinary optical transmission through sub-wavelength hole arrays," Nature 391:667-669, Feb. 12, 1998.

Ferry et al., "Light trapping in ultrathin plasmonic solar cells," Optics Express 18(S2), Jun. 21, 2010, 9 pages.

Hacia et al., "Detection of heterozygous mutations in BRCA1 using high density oligonucleotide arrays and two-colour fluorescence analysis," Nature Genetics 14:441-447, Dec. 1996.

Kohane et al., Microarrays for an Integrative Genomics, MIT Press, 2003, pp. 69-88.

Koller et al., "Organic plasmon-emitting diode," Nature Photonics 2:684-687, Nov. 2008.

Lal et al., "Nano-optics from sensing to waveguiding," Nature Photonics 1:641-648, Nov. 2007.

Le et al., "Plasmons in the Metallic Nanoparticle-Film System as a Tunable Impurity Problem," Nano Letters 5 (10):2009-2013, 2005.

Morris et al., "A Versatile Semiconductor Platform for Chemical and Biological Sensing (Poster)," Integrated Plasmonics Corporation, Palo Alto, CA, Nov. 16, 2011.

Narayan et al., "Novel strategies for polymer based light sensors," Thin Solid Films 417:75-77, 2002.

Palik (ed.), Handbook of Optical Constants of Solids III, Academic Press, 1998, 9 pages.

Raether, Surface Plasmons on Smooth and Rough Surfaces and on Gratings, Springer Tracts in Modern Physics 111:1-133, 1988.

Sonnichsen et al., "A molecular ruler based on plasmon coupling of single gold and silver nanoparticles," Nature Biotechnology 23(6):741-745, Jun. 2005.

Thrush et al., "Integrated bio-fluorescence sensor," Journal of Chromatography A, 1013:103-110, 2003.

Walters et al., "A silicon-based electrical source of surface plasmon polaritons," Nature Materials 9:21-25, Jan. 2010.

* cited by examiner

INTEGRATED PLASMONIC NANOCAVITY SENSING DEVICE

FIELD OF THE INVENTION

The invention generally relates to integrated plasmonic devices and, in particular, though not necessarily, to an integrated plasmonic nanocavity sensing device and a plasmonic sensor pixel array comprising such devices.

BACKGROUND OF THE INVENTION

Many existing biological and chemical sensors detect the presence or absence of target material in the vicinity of the sensor based on changes in the propagation of electro-magnetic radiation. Such sensors have previously been fabricated using dielectric waveguide components on the basis of silicon-on-insulator (SOI) wafers and using metallic surfaces that support surface plasmon polaritons, i.e. electromagnetic excitations at a metal-dielectric interface. While such sensors will typically meet sensitively requirements for useful sensors, their dimensions are limited by diffraction effects in the dielectric waveguide components used and by the coherence length of surface plasmon polaritons, which limits the area on a metal surface that can considered to represent an independent measurement. Such sensors can be therefore less attractive for integration with silicon based electronic components, which are many times smaller.

For example WO2009/112288 describes plasmonic sensing devices that are based on "extraordinary optical transmission" (EOT) phenomena in which the normalized transmission cross-section of sub-wavelength holes or slits arranged in an array exceeds that of a single sub-wavelength hole or slit. These effects have been extensively studied since the first report of Ebbesen, et al., in Nature, February 1998. The EOT effect can be attributed to resonances between light that is directly transmitted through the holes and light that is scattered into and out of surface waves by the sub-wavelength features, in some cases including surface plasmon polaritons that are confined to the exterior metal-dielectric interfaces of the structure supporting EOT.

One problem with EOT plasmonic sensing devices is that they will be subject to constraints deriving from the coherence length of single interface propagating surface plasmons, which is typically of the order of a few micrometers. A second problem with such devices is that they will require at least two scattering centers to establish the interference condition necessary for EOT. Hence in order to accomplish EOT effects typically an EOT-supporting metallic grating (e.g. an array of plasmonic scattering centers provided in a metallic layer or multilayer) of relatively large dimensions is needed so that a high integration density cannot be accomplished.

A further plasmonic sensing device is described in U.S. Pat. No. 7,599,066. This document describes a sensor that relies on detecting absorption features associated with the localized plasmon resonance of nano-sized metallic particles. Such particles however are irregularly shaped and thus not very well defined resulting in deterioration of the resonant response of the sensor. Moreover, the irregularly will also affect the uniformity of the sensors when fabricated as dense sensor arrays on a wafer.

More recently, alternative waveguide structures that support surface plasmon polariton-like modes have been developed consisting of metal-dielectric-metal waveguide structures, such as those described by Dionne, et al., Physical Review B 73, 035407, 2006. These excitations propagate with an effective wavelength that is smaller than the effective wavelength of surface plasmon polaritons that are supported by a single metal-dielectric interface of the same frequency. Such metal-dielectric-metal waveguide structures further allow for electrically driven discrete devices for generating surface plasmons. Such devices are known for example from the article by Walters et. al., "A silicon-based electrical source of surface plasmon polaritons", Nature Materials, 6 Dec. 2009.

Hence, improvements are needed in order to achieve integrated plasmonic sensing devices based on localized plasmon resonance mechanisms. In particular, improvements are needed for the realization of integrated plasmonic sensing devices based on well-defined localized plasmon resonances, wherein the formation of the sensing devices is compatible with CMOS fabrication and wherein the formation allows dense integration of sensitive biological and chemical sensors and other optical spectroscopy tools on a silicon wafer.

SUMMARY OF THE INVENTION

It is an object of the invention to reduce or eliminate at least one of the drawbacks in the prior art. In one aspect, the invention may relate to an integrated plasmonic sensing device, wherein said device may comprise: at least one optical source comprising a first conductive layer and a second conductive layer, and an active optical source layer between at least part of said first and second conductive layers; at least one nanocavity extending through said first and second conductive layers and said active optical source layer, wherein said optical source is configured to generate surface plasmon modes suitable for exciting one or more resonances in said nanocavity; and, at least one optical detector comprising at least one detection region formed on said substrate in the vicinity of said nanocavity resonator, wherein said optical detector is configured to sense excited resonances in said nanocavity.

The structure of the integrated plasmonic sensing device allows dense integration of active plasmonic devices such as optical sources and optical detectors together with plasmonic elements such as waveguides and nanocavity resonators. Plasmonic nanocavity resonators are optical resonators constructed from combinations of dielectric and metallic materials that support electromagnetic modes at resonance frequencies corresponding to free-space wavelengths between approximately 200 nm and 2 um, in which the mode volume is less than approximately 1 cubic free-space wavelength. Moreover, the structure is compatible with CMOS architectures.

In one embodiment said plasmonic sensing device may comprise a nanocavity, wherein the electromagnetic fields supported by said nanocavity at resonance extend at least a part into the detection region of said detector such that the coupling between said plasmon resonances and said optical detector is maximized.

In another embodiment said first and second conductive layer may be formed out of a metal, preferably selected from the group comprising aluminum, silver, copper and gold and/or alloys thereof. The structure comprises metal-dielectric-metal structures which may be used in the fabrication of an optical source or, alternatively, as a waveguide for transmitting plasmons from an optical source to another plasmonic element and/or active device.

In further embodiment said active optical source layer may comprise nanocrystals and/or defect centers, preferably said nanocrystals and/or defect centers being embedded in a silica, silicon nitride, silicon carbide, or alumina host. In yet a further embodiment said detecting region may comprise at least one depleted semiconducting region, preferably a pn type junction and/or a Schottky type junction. In a further embodiment, said detector may comprise a CMOS detector. The detector area may be integrated in the silicon support substrate so that the detecting area and/or other plasmonic devices may be directly coupled to driving- and/or sensing electronics integrated at the location of the plasmonic sensing device.

In one variant the geometry of at least part of said at least one nanocavity may comprise a substantially rectangular cavity, an annular cavity and/or combinations thereof. The plasmonic resonator may be realized as a nanocavity which extends through the metal-dielectric-metal structure so that coupling of the nanocavity and the optical source may be achieved. The nanocavity may be realized by ion beam sputtering, chemical etching, and/or lift-off processes thereby allowing a large variation of different cavity configurations.

In another variant said integrated plasmonic sensing device may further comprise: one or more integrated electronic circuits comprising one or more electronic devices formed in n-type or p-type wells, preferably CMOS-type integrated electronic circuits, said one or more integrated electronic circuits being configured for driving said optical source and/or said optical detector and/or for processing one or more detector signals originating from said at least one optical detector.

In yet another variant said at least one or more parts of said first and/or second conductive layers may be used as metal interconnect areas for electrically connecting said optical source to said one or more integrated electronic circuits. Parts of the layers used for fabricating the integrated plasmonic sensing device may advantageously be used for simultaneous realization of metallic interconnects or vias for connecting the CMOS electronic devices to the optical source and/or the optical detector in the plasmonic sensing device.

In a further variant said one or more integrated electronic circuits may be configured to operate said optical source. In yet a further variant said optical source may be operated in a pulsed-mode wherein an output signal is determined on the basis of a first detector signal that is measured without activating the optical source and a second detector signal that is measured when activating the optical source. Using such pulse-mode operation of an integrated plasmonic sensing device allows improvement of the signal-to-noise ratio.

In a further aspect, the invention may relate to a plasmonic sensor pixel array, comprising a plurality of plasmonic pixel sensors, each plasmonic pixel sensor comprising at least part of an integrated plasmonic sensing device according to any of the embodiments as described above.

In one embodiment said plasmonic sensor pixel array may further comprise: one or more dielectric layers formed over at least part of said plasmonic pixel sensors, said one or more dielectric layers comprising one or more microchannels in contact with at least part of said nanocavities associated with said plasmonic pixels sensors, said microchannels being configured to guide a fluid and/or gas into or through said nanocavities.

The invention will be further illustrated with reference to the attached drawings, which schematically show embodiments according to the invention. It will be understood that the invention is not in any way restricted to these specific embodiments.

DETAILED DESCRIPTION

Figure 1:
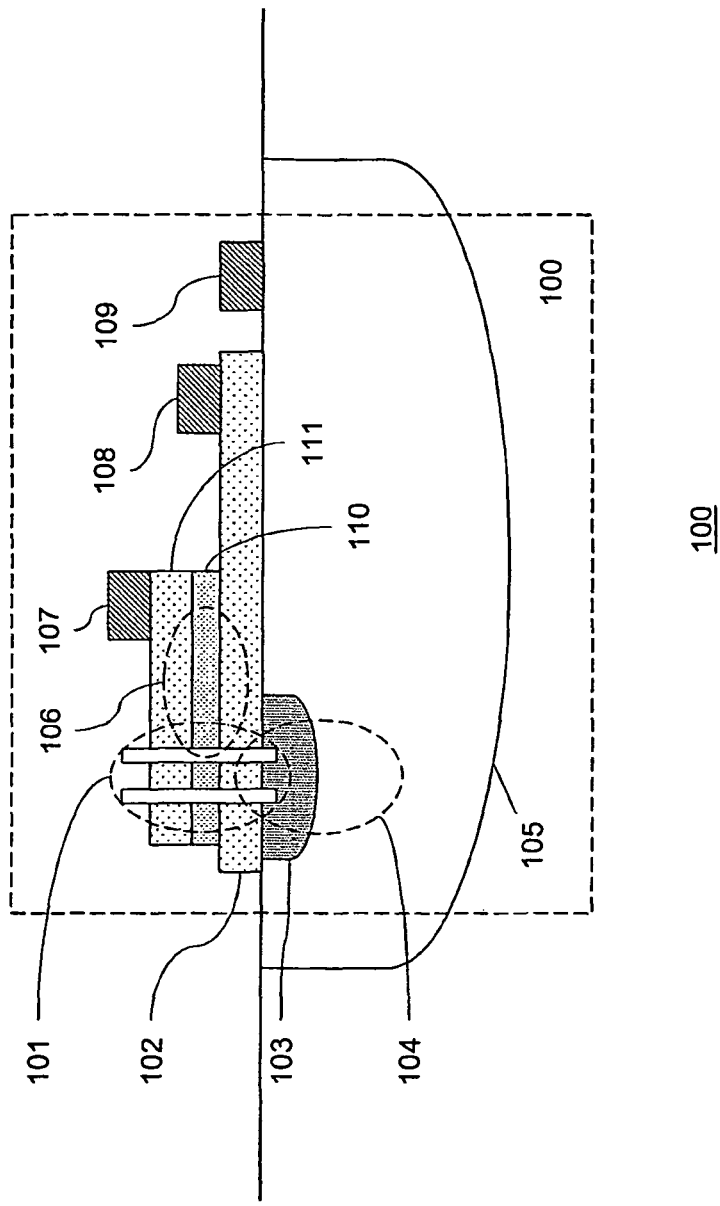
FIG. 1 depicts an integrated plasmonic device according to one embodiment of the invention.

FIG. 1 is a schematic diagram showing a cross section of an integrated plasmonic sensing device 100 according to one embodiment of the invention. The integrated device may comprise a plasmonic nanocavity resonator 101, i.e. a sub-micron sized cavity configured for supporting localized resonant plasmonic modes inside the cavity, combined with an integrated optical source 106 and an integrated detector 104. In this non-limiting example, the resonant cavity 101 may be driven by the optical source 106, in particular guided surface plasmons generated by said optical source. To that end, the optical source 106 may comprise a conductive top and bottom layers 111, 102 forming the electrical contacts of the source. The conductive layers may relate to thin-film metal layers, in particular low-resistance thin-film metal layers, such as aluminum, copper, silver or gold having thickness within the range between 5 and 500 nm. In the example of FIG. 1 the conductive top layer may relate to a gold contact of 250 nm thickness and an aluminum bottom contact layer 102 of 100 nm thickness.

At least part of an intermediate layer 110, typically a dielectric intermediate layer, between the top and bottom layers may comprise active optical source layer 110a. The thickness of the optical layer is within the range between 5 and 500 nm. In particular, the thickness of the optical layer is selected such that the multilayer structure formed by the conductive top and bottom layers and the intermediate layer form a plasmonic waveguide for transmitting guided surface plasmons generated in the active optical source layer to the plasmonic nanocavity resonator.

The thickness of the metal-dielectric-metal plasmonic waveguide is additionally selected to provide single mode operation at excitation frequencies, e.g. when the contact layers are composed of gold and aluminum and the index of refraction of the optically active source layer is approximately 1.8, the layer thickness may be chosen to be less than approximately 180 nm for single plasmon mode operation at frequencies corresponding to free space wavelengths of approximately 800 nm. Single mode operation is provided when the dielectric layer of the MDM plasmonic waveguide is too thin to support propagating transverse electric (TE) modes and higher order transverse magnetic (TM) modes that do not resemble surface plasmon polaritons, i.e. too thin to support photonic modes.

The dimensions and materials used in a MDM plasmon waveguide structure are particularly selected so that the waveguide supports a TM mode having two local maxima in field intensity at the metal-dielectric interfaces surrounding the dielectric layer of the MDM structure. This plasmonic waveguide mode has a symmetric magnetic field profile about the center of the waveguide in the direction perpendicular to the direction of propagation for symmetric material geometries. Such modes are thus different from surface plasmon modes supported by single metal-dielectric interfaces which are used in EOT based sensing devices and in conventional surface plasmon resonance sensors. In one embodiment, the active optical source layer may comprise a plurality of semiconductor nanocrystals or related defect centers embedded in an insulating host material, e.g. silicon nanocrystals embedded in silica or in an alumina host material. Such optically active materials may be grown by known deposition techniques, including atomic layer deposition (ALD) and/or low-pressure chemical vapor deposition (LPCVD) techniques. Other types of optically active materials include optically doped materials, e.g Er or other elements in a host material, doped semiconductors and/or junctions composed of layers based on inorganic and organic materials well known in the art.

In the example of FIG. 1, the optical source layer may comprise a multilayer stack of alternating layers of alumina and optically active silicon nanocrystals. In particular, the optically active silicon nanocrystals may have diameters between 2 nm and 10 nm. This optically active material comprising a silicon nanocrystal doped alumina layer may be obtained by sequential ALD of alumina and LPCVD of silicon nanocrystals. In this manner, layers of alumina and nanocrystals may be deposited without breaking vacuum to form an optical source layer having a thickness of approximately 100 nm.

An MDM waveguide comprising a silicon nanocrystal-doped alumina layer of approximately 100 nm thickness having gold metal layers may support only one propagating guided surface plasmon mode. This transverse magnetic (TM) mode is characterized by a magnetic field with a normal component (Hy) that is symmetric across the center of the waveguide. The mode may have a characteristic propagation length that depends on the frequency of the excitation, e.g. 3-5 micrometers for emission range corresponding to free space wavelengths between 600 nm and 900 nm, as is typical for Si nanocrystals in alumina.

In the particular device layout of FIG. 1, the layers forming the source are formed on a substrate, typically a silicon based substrate 112, allowing the formation of a detecting region 104 associated with a detector, wherein the detecting region is positioned in the vicinity of, preferably underneath, the nanocavity resonator. In FIG. 1 the detecting region is formed of a shallow junction diode formed of a p-doped region 103 within an n-well 105 on a p-type silicon substrate.

Electrical contacts 107, 108, and 109 are connected respectively to top contact 111, bottom contact 102, and the n-well 105. When a sufficient voltage (typically in the range between 2 V and 20 V) is applied between electrical contacts 107 and 108, charge carriers may be driven through the optically active source layer 110. These charge carriers may excite the optically active source layer, e.g. impact excitation processes can create confined excitons in the embedded silicon nanoparticles at an applied voltage of approximately 10 V. These excitons may decay by transferring energy to modes supported by the metal-dielectric-metal (MDM) plasmonic waveguide comprised of top contact 111, active optical source layer 110, and bottom contact 102.

For example, in an MDM waveguide comprising a silicon nanocrystal-doped alumina layer of approximately 100 nm thickness having gold metal layers, excitons in the silicon nanocrystals may decay by radiative dipole transitions only by direct near-field coupling to the single propagating guided surface plasmon mode.

Thus source 106 comprises an electrical source of electromagnetic radiation in the form of guided surface plasmons suitable for exciting the plasmonic nanocavity resonator 101. In an exemplary embodiment, source 106 may provide an excitation by an approximately Gaussian spectrum centered at 800 nm having a spectral full-width-at-half-maximum (FWHM) of approximately 100 nm. By selecting the appropriate optically active materials in the active optical source layer 110 excitation sources at frequencies spanning a range of free-space wavelengths between approximately 200 nm and 2 um may be realized.

The plasmonic nanocavity resonator 101 may be impedance matched to source 106 so that the power generated by the optical source may be efficiently transferred to the nanocavity resonator. The nanocavity 101 may have an opening at the top surface allowing the cavity to be filled with a particular material. Changes in the dielectric material composition may change the efficiency of power transfer to the detecting area, thus providing a first mechanism for sensing changes in the material composition of nearby regions.

Hence, the localized plasmon resonant modes supported by nanocavity 101 may transfer power to the integrated detector 104 by radiation in the direction of the detector or by near-field interaction between the evanescent tail of the mode and the detecting volume (i.e. the electric field of the localized mode may extend into the photoelectric absorbing layer of the detector).

In both cases, charge carriers are excited in the detector 104 when the plasmon resonant modes supported by nanocavity 101 are excited. The efficiency of power transfer from nanocavity 101 to integrated detector 104 may also vary with changes in the composition of the material in the vicinity of the nanocavity thereby providing a second mechanism for sensing. The photo-excited carriers created in detector 104 are measured by a change in current or voltage between contacts 102 and 105 to infer the sensor state.

From the above it follows that in contrast with known plasmonic sensing devices (e.g. plasmonic sensing devices based on an EOT supporting metallic grating), the integrated plasmonic sensing device as depicted in FIG. 1 is configured to generate a localized plasmon resonance in the nanocavity. Hence, as the plasmon resonance is localized to a single cavity dense integration of such plasmonic sensing devices may be achieved.

In some embodiments, the resonant nanocavity can be designed to additionally couple power between the resonator and the far-field away from the integrated detector and the device substrate. Light from the far-field from a laser or other external source can act as an excitation source for the localized plasmon resonant modes supported by nanocavity 101. In this configuration, the integrated detector can monitor the response of the plasmonic cavity to the external excitation. Alternatively, light radiated from the plasmonic nanocavity can be collected and monitored. For example, light radiated from the cavity can be collected with a microscope and the spectrum of the radiated light can be measured with a spectrograph and external detector to observe characteristic nanocavity resonances. These designs are useful in test and prototype devices intended to demonstrate operational principles of the invention.

Biological or chemical binders may be attached to the exposed surfaces of the nanocavity to improve the sensitivity and specificity of the sensing response. These binders may be unlabeled or labeled by one or more stains, markers, or dyes, including fluorescent dyes. Said sensitive materials may be deposited using a variety of techniques known in the art, including, but not limited to, array printing by screen or ink-jet methods, spin, spray, or draw coating, and/or vapor deposition. These agents will have the greatest effect on the power matching conditions of the cavity when positioned in regions of high mode intensity. Substances to be analyzed can be delivered to the sensor by diffusion or directed flow, in some cases using microfluidic technology wherein microchannels for transporting fluids may be fabricated over the integrated plasmonic devices and in contact with the nanocavity and/or within the nanocavity. In some embodiments, adjacent similar sensors may be used to provide reference signals. Care must be taken to suitably insulate components of the sensor that are not electrically neutral during measurement in case possible current flows through conductive materials in the vicinity of the detector.

In some embodiments, sensing of secondary stimulus can be accomplished by placing a material sensitive to said secondary stimulus in the vicinity of the plasmonic nanocavity. For example, a material in which the index of refraction changes with temperature can be used to implement a temperature sensing modality. In other embodiments, the sensing of a secondary stimulus is accomplished by a change in the geometry of the plasmonic nanocavity. For example, stress induced change in nanocavity geometry can be used to implement a strain sensing modality.

In some embodiments, the sensed material itself may be optically active. For example, a material which absorbs light at the excitation frequency and later emits light at a second frequency which couples power from the integrated optical source to the integrated detector. In some embodiments, the sensed material may be a fluorescing molecule within the plasmonic nanocavity that is excited by the integrated optical source and later emits light at a lower frequency that is detected by the integrated detector.

In contrast to known dielectric microcavity resonators, plasmonic nanocavity resonators may have relatively low resonance Q values, typically less than around 100. This implies that the intrinsic sensitivity of integrated plasmonic sensors may be lower than dielectric microcavity sensors. In an un-optimized exemplary embodiment, the intrinsic response is approximately 100% per refractive index unit near a refractive index of 1.3. The detection threshold for such an embodiment however may still compete favorably with dielectric microcavity alternatives, provided that the integrated source is sufficiently stable and the integrated detector exhibits sufficiently low noise performance. In many cases, the device performance will be substantially determined by the stability of the integrated source.

It is clear for a skilled person that other integrated plasmonic devices than the one depicted in FIG. 1 may be realized without departing from the invention. For example, an integrated plasmonic device may comprise several nanocavities coupled to one plasmonic source. Other implementations may relate to one nanocavity coupled to several sources wherein each source may be individually addressed by the driving electronics for generating plasmons at different excitation frequencies.

The benefits of using a plasmonic resonant nanocavity include a smaller possible resonator volume and hence a smaller sensor footprint, better fabrication compatibility with other circuit technologies of interest, improved signal-to-noise ratio and greater potential for dense on-chip integration through the use of local, co-fabricated sources and detectors.

Figure 2:
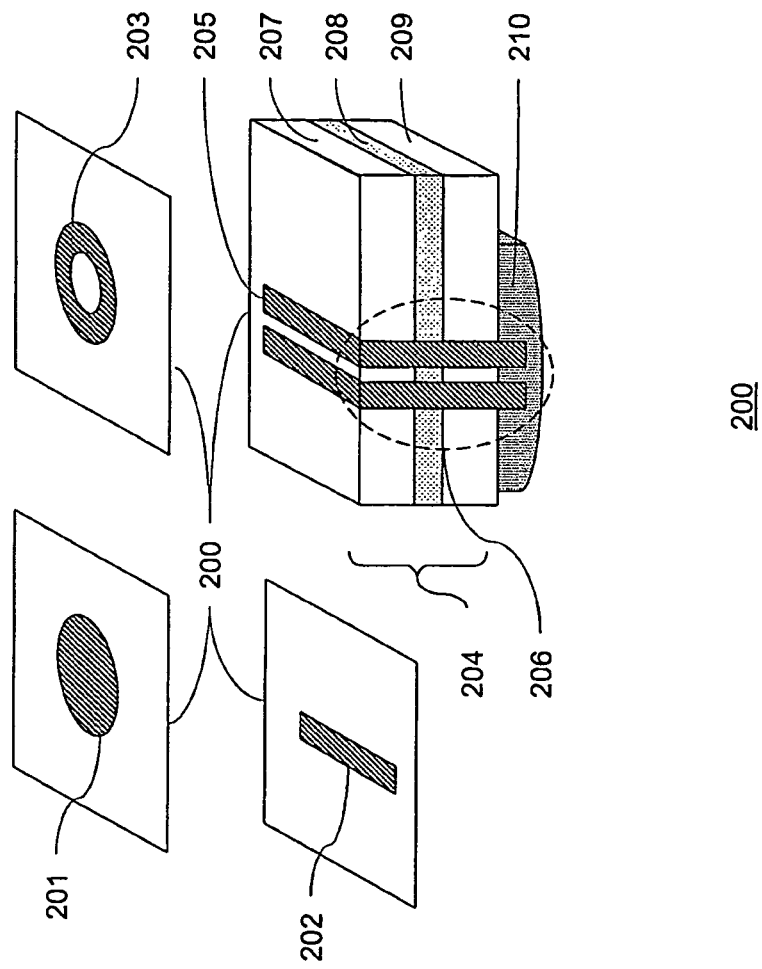
FIG. 2 depicts exemplary nanocavity resonator geometries according to various embodiments of the invention.

FIG. 2. depicts exemplary plasmonic nanocavity resonator geometries according to various embodiments of the invention. The geometries are visualized from the top of the sensor in the plane of top contact layer 200. Cut-away 204 indicates the depth of the nanocavity 206, which extends through top contact 207, active optical source layer 208, and bottom contact 209. In an exemplary embodiment, the plasmonic nanocavity 206 may extend into the substrate, in particular the sensing area of a detector, e.g. the acceptor of an underlying pn-diode detector 210. It may be preferable to minimize the extension of the nanocavity into the substrate such that a maximum coupling between the cavity and the detector is achieved. In other embodiments it may be preferable to optimize the extension of the nanocavity into the substrate to maximize the coupling between the plasmonic nanocavity resonator and far-field radiation.

A circular cavity 201, typically having diameter between 20 nm and 2000 nm and depth between 10 nm and 1000 nm, has optimal transmission in the direction of the integrated detector for radiation corresponding to a free space wavelength of 800 nm when the diameter is approximately 300 nm. Such circular cavities will couple to light in all polarization directions about the surface normal due to the symmetry of the device. In contrast, a linear slot geometry 202, typically having slot length between 200 nm and 2000 nm, slot width between 5 nm and 500 nm, and depth between 10 nm and 1000 nm, will couple to linearly polarized light. Coaxial geometry 203, with typical inner radius between 5 nm and 500 nm, typical outer radius between 20 nm and 2000 nm, and typical depth between 10 nm and 1000 nm, and adjacent slot geometry 205, with typical slot length between 200 nm and 2000 nm, slot width between 5 nm and 500 nm, slot separation between 5 nm and 500 nm, and typical depth between 10 nm and 1000 nm, can have improved performance in comparison to simpler geometries.

In an exemplary embodiment, such plasmonic nanocavity geometries are fabricated by removing material using focused ion beam milling. Alternative fabrication methods may include masked chemical etching, three-dimensional lithography, lift-off, or imprint methods. "Bulls-eye" and grating geometries follow as a straightforward extension of these designs, however these larger nanocavity geometries may compromise the small device footprint specific to the invention.

Figure 3:
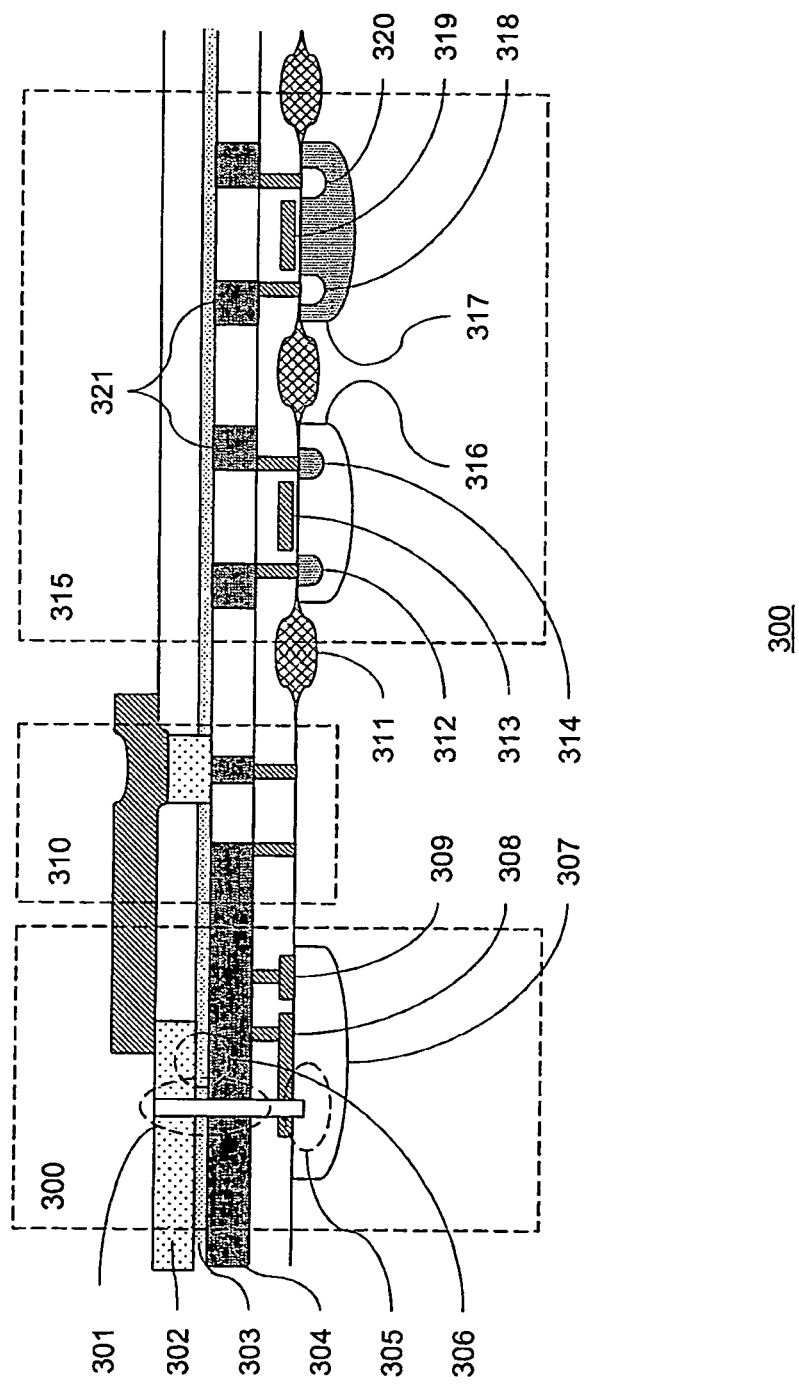
FIG. 3 depicts a schematic of an integrated plasmonic device according to another embodiment of the invention.

FIG. 3 depicts a schematic of an integrated plasmonic device according to another embodiment of the invention. In particular FIG. 3 shows a schematic cross section of an integrated circuit in which one representative plasmonic nanocavity sensor 300, is connected via metallization layers 310 to underlying logic, detection, and driving CMOS electrical circuits 315. Here conductive layers forming the top contact layer 302 and the bottom contact layer 304 of sensor 300 may be composed of aluminum, copper, or gold. Active optical source layer 303 may be composed of an optically active material such as silicon nanoparticles in an alumina host. These layers together comprise optical source 306.

Moreover, bottom contact layer 304 and top contact layer 302 may be part of metallization structures that simultaneously define interconnects 321 and later interconnect stages as depicted for example in sensor interconnect region 310. The conducting layers forming the contacts of the plasmonic source and the interconnect metallization regions may be formed using an aluminum or copper damascene type metallization process well known in the art. Such a metallization process uses etching of trenches (vias) in an insulating inter-layer, filling the trenches with a metal layer (e.g. aluminum or copper) and polishing the metal layer back to the surface of the inter-layer so that metal interconnects (metallizations) are formed in the inter-layer.

Plasmonic nanocavity 301 is depicted as a single slot extending through the conductive layers and the optically active layer associated with the optical source towards the substrate n-well 307. In this example integrated detector 305 may be a Schottky diode formed by detector contact 308 and n-well 307. Detector contact 308 may be electrically connected to bottom contact layer 304, while n-well back contact 309 may provide a reference voltage for the detection circuit. As shown in sensor interconnect region 310, each sensor in the plurality can be connected to underlying interconnect layers that lead to CMOS electrical circuits 315. Underlying CMOS circuits 315 can include n-wells 316 and p-wells 317, separated by field oxide regions 311. Transistor gates 313 and 319 control channels between source regions 312 and 318 and drain regions 314 and 320. These CMOS electrical circuits can provide drive currents for source 306, amplification and readout for detector 305, and additional logic and interface functionality.

In one embodiment, the integrated electrical circuitry associated with the plasmonic sensing pixel sensor is configured to operate the optical source and detector in a pulsed-mode. In such pulsed-mode, the plasmonic sensing pixel is controlled to determine a pixel output signal which is determined on the basis of a first detector signal measured without activating the optical source and a second detector signal measured when activating the optical source. Using such pulse-mode operated integrated plasmonic sensing device allows improvement of the signal-to-noise ratio.

A key enabling factor for an exemplary embodiment is the CMOS backend compatible fabrication of sensor 300 using low temperature processes. These low temperature processes may be used in combination with damascene type metallization processes. Such metallization processes allow sufficiently flat inter-layers for the formation of the optically active layer. In the exemplary embodiment, optically active layer 303 may be formed using a combination of low pressure chemical vapor deposition (LPCVD) and atomic layer deposition (ALD) at a substrate temperature of 325 C.

The integrated plasmonic device 300 may be used as a unit cell, i.e. a plasmonic sensing pixel, for use in an array of such devices aligned in rows and columns wherein driving lines for individually driving the one or more optical sources and the one or more detectors in each pixel, and sensing lines coupled to the output of the one or more detectors are used to address pixels and to obtain a sensing output thus addressing the plasmonic sensing pixels.

When a plurality of sensors is present, the resulting integrated sensing circuit may function as an imaging sensor providing spatial information describing the distribution of sensed materials. Cross-talk between sensors is negligible due to the close localization of the electromagnetic modes within each of the plasmonic nanocavity sensors in the circuit. Different regions of the integrated sensing circuit may be designed to sense different chemical or biological materials, by incorporating a plurality of binder materials, which could be applied by micro-droplet array printing to the integrated sensing circuit. The geometry of the plasmonic nanocavity, or the composition of the integrated source or the integrated detector may also vary with location in the integrated sensor circuit to enable multiple detection modalities.

Figure 4:
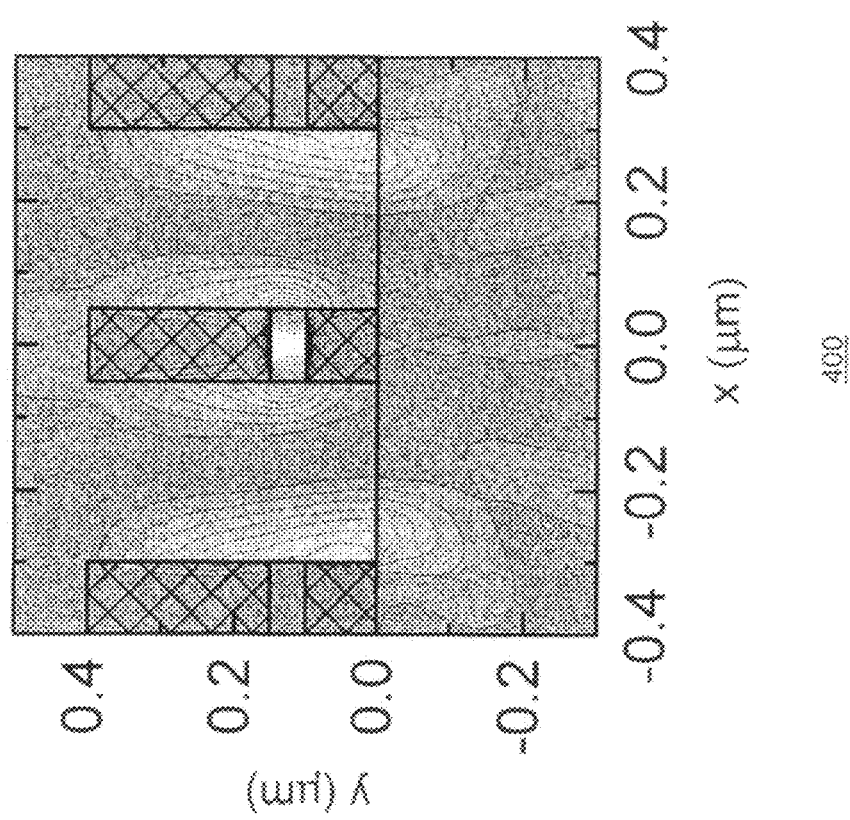
FIG. 4 depicts an exemplary magnetic field profile for a localized electromagnetic mode supported by a plasmonic nanocavity resonator.

FIG. 4 depicts an exemplary magnetic field profile for a localized electromagnetic mode supported by a plasmonic nanocavity resonator. Gray scale fill and indicated contour lines represent the time-averaged magnitude of the $H_z$ component of the magnetic field at each point in the cross section, as simulated using two dimensional full field FDTD techniques in which source power is injected at a frequency of 360 THz into the guided surface plasmon mode supported by the adjacent MDM waveguide. These two dimensional simulations adequately model the performance of physical MDM waveguides that must have a finite width in the direction perpendicular to the intended mode propagation direction. Finite width MDM waveguides provide additional confinement that is advantageous for densely integrated devices. It is evident that the excited mode is localized to a sub-micron region within the resonant cavity. It is also evident that the resonance is unrelated to interference effects between adjacent nanocavities or scattering centers. This localized plasmon resonant mode is thus different from surface plasmon resonances used in EOT-based sensing devices. The simulated geometry consists of two adjacent rectangular cavities defined by removing material from a metal-insulator-metal waveguide structure having a gold top contact layer of 250 nm thickness, an aluminum bottom contact layer of 100 nm thickness, and an alumina insulator layer of 50 nm thickness. Each rectangular cavity is 150 nm wide in the x direction and 400 nm long in the y direction, so that the bottom of the cavity is coincident with the top of the underlying silicon substrate. The rectangular cavities and half plane above the nanocavity are filled with a uniform dielectric having a refractive index of 1.5 in order to demonstrate the power matched condition at the excitation frequency of 360 THz, which corresponds to a free space wavelength of approximately 830 nm. The two rectangular cavities are separated by 100 nm. This structure couples more than 40% of incident power launched in the guided surface plasmon mode from the MDM waveguide to the underlying detection region when the excitation frequency is matched to the nanocavity mode.

Figure 5:
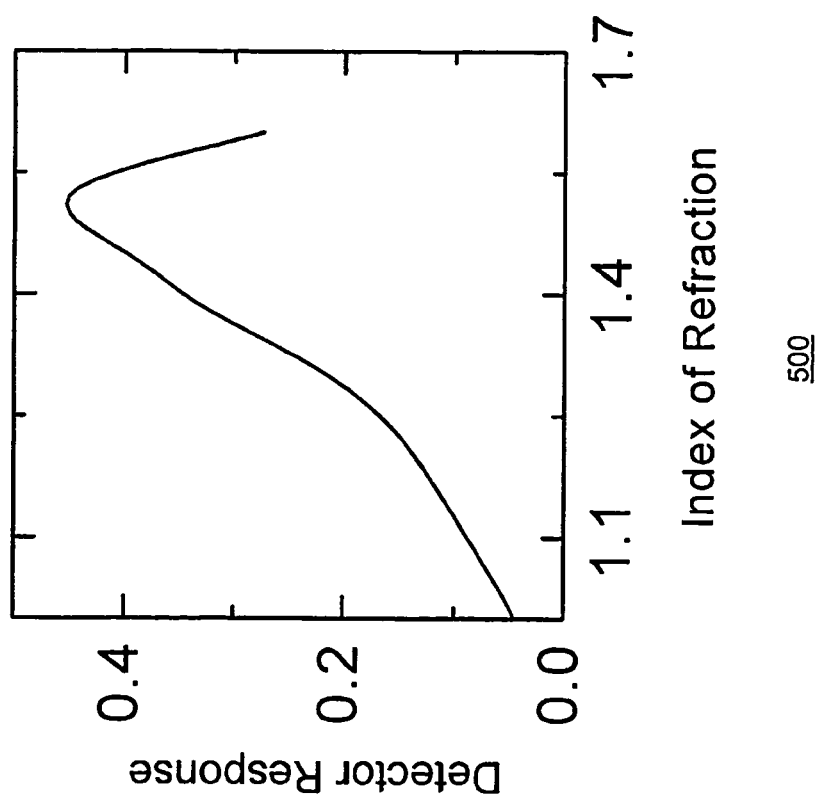
FIG. 5 depicts a graph of the power sensed by the sensor versus the index of refraction within an exemplary nanocavity resonator.

FIG. 5. depicts a graph of the power sensed by the sensor versus the index of refraction within a nanocavity. In particular it shows that the power coupled to the underlying detection region changes when the index of refraction within the plasmonic nanocavity is changed away from the matching condition at an index of 1.5. For this geometry, a maximum slope of approximately 150% per refractive index unit is observed, near a refractive index of approximately 1.3. This demonstrates the operational principle of the sensor whereby changes in the material composition of regions in the vicinity of the sensor may modify the efficiency of power transfer to the integrated detector, resulting in an electrical response.

Figure 6:
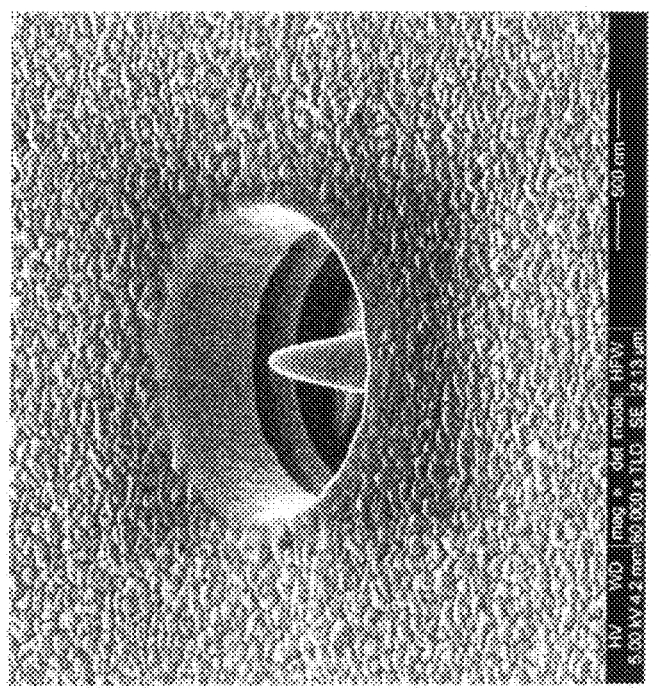
FIG. 6 depicts a scanning electron microscope image of an exemplary nanocavity resonator fabricated using focused ion beam etching.

FIG. 6 depicts a scanning electron microscope image of an exemplary nanocavity resonator fabricated using focused ion beam etching. This image is collected at a viewing angle of 52 degrees with respect to the sample normal and depicts an annular nanocavity resonator with an inner diameter of approximately 100 nm and an outer diameter of approximately 900 nm. The characteristic grain structure of the gold contact layer is evident in the surface surrounding the nanocavity. The nanocavity is milled through the optical source and MDM waveguide, together comprising a gold top contact of approximately 300 nm thickness, a 50 nm optically active layer comprising silicon nanocrystals in alumina, an approximately 80 nm thick aluminum layer, and a Ti/W diffusion barrier layer of approximately 20 nm thickness. Such a diffusion barrier is well known in the art, and is typically formed to prevent the growth of pyramidal spikes of aluminum-silicon alloys that may otherwise cause electrical shorts in the pn diode. At the bottom of the nanocavity, some unintentional undercutting into the silicon diode detector beneath the nanocavity is evident.

Figure 7:
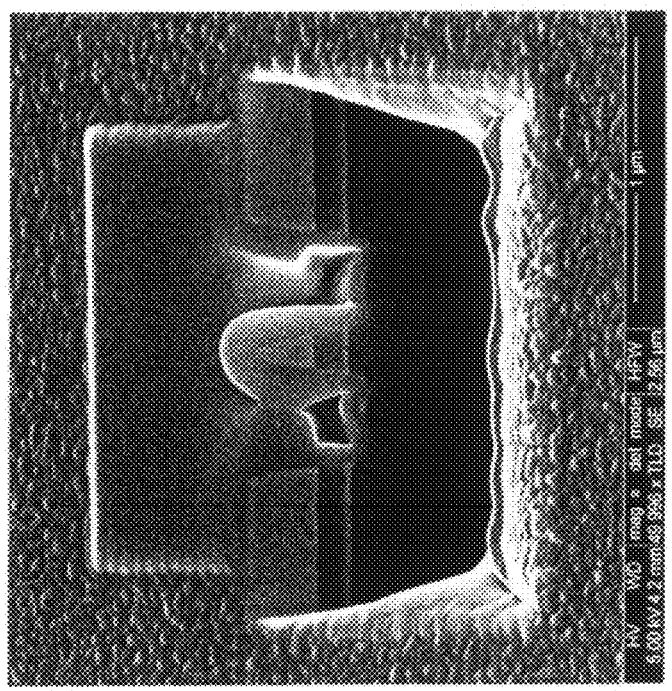
FIG. 7 depicts a scanning electron microscope image of an exemplary nanocavity resonator fabricated using focused ion beam in cross section.

FIG. 7 depicts a scanning electron microscope image of an exemplary nanocavity resonator fabricated using focused ion beam in cross section. This image is collected at a viewing angle of 52 degrees with respect to the sample normal and depicts an annular nanocavity resonator with an inner diameter of approximately 100 nm and an outer diameter of approximately 900 nm. The cross section is prepared by first depositing platinum through an electron beam assisted deposition process, as is well known in the art, and then milling a cleaning cross section using the focused ion beam to expose a cut away view approximately through the center of the nanocavity. This micrograph shows that the nanocavity extends through the layers comprising the optical source and MDM waveguide, including a gold top contact of approximately 300 nm thickness, a 50 nm optically active layer comprising silicon nanocrystals in alumina, an approximately 80 nm thick aluminum layer, and a Ti/W diffusion barrier layer of approximately 20 nm thickness. In this image, the contract between the optically active layer and the aluminum layer is less clear. The thin layer of high apparent brightness is the Ti/W diffusion barrier. At the bottom of the nanocavity, some unintentional undercutting into the silicon diode detector beneath the nanocavity is evident.

It is to be understood that any feature described in relation to any one embodiment may be used alone, or in combination with other features described, and may also be used in combination with one or more features of any other of the embodiments, or any combination of any other of the embodiments. Moreover, the invention is not limited to the embodiments described above, which may be varied within the scope of the accompanying claims.

The invention claimed is:

1. An integrated plasmonic sensing device comprising:
   a plasmonic waveguide disposed on a substrate, said plasmonic waveguide comprising a first conductive layer and a second conductive layer and a dielectric layer between said first and second conductive layer, wherein at least part of said dielectric layer is configured as an optical source for exciting surface plasmon modes supported by said waveguide;
   at least one nanocavity extending through said first and second conductive layers and said dielectric layer, wherein said waveguide is configured to couple said surface plasmon modes to said nanocavity for activating one or more localized plasmon resonances in said nanocavity; and,
   at least one optical detector comprising at least one detection region formed on or in said substrate in the vicinity of said nanocavity, wherein said optical detector is configured to sense said one or more localized plasmon resonances in said nanocavity.

2. Integrated plasmonic sensing device according to claim 1, wherein electromagnetic fields supported by said nanocavity at resonance extend at least a part into the detection region of said detector.

3. Integrated plasmonic sensing device according to claim 1, wherein said first and second conductive layer is formed out of a metal, preferably selected from the group comprising aluminum, silver, copper and gold and/or alloys thereof.

4. Integrated plasmonic sensing device according to claim 1, wherein said optical source includes an optical active layer comprising optically activated nanocrystals and/or defect centers, said nanocrystals and/or defect centers embedded in a silica or alumina host.

5. Integrated plasmonic sensing device according to claim 1, wherein said detecting region comprises at least one depleted semiconducting region comprising a pn type junction and/or a Schottky type junction.

6. Integrated plasmonic sensing device according to claim 1, wherein the geometry of at least part of said at least one nanocavity comprises a substantially rectangular cavity, an annular cavity and/or combinations thereof.

7. Integrated plasmonic sensing device according to claim 1 further comprising:
   one or more integrated electronic circuits comprising one or more electronic devices formed in n-type or p-type wells of CMOS-type integrated electronic circuits, said one or more integrated electronic circuits being configured for driving said optical source and/or said optical detector and/or for processing one or more detector signals originating from said at least one optical detector.

8. Integrated plasmonic sensing device according to claim 7, wherein at least one or more parts of said first and/or second conductive layers are used as metal interconnect areas for electrically connecting said optical source to said one or more integrated electronic circuits.

9. Integrated plasmonic sensing device according to claim 7, wherein said one or more integrated electronic circuits are configured to operate said optical source and/or said optical detector.

10. Integrated plasmonic sensing device according to claim 7, wherein at least part of said integrated electronic circuits are configured to produce an output signal which is determined on the basis of a first detector signal measured without activating the optical source and a second detector signal measured when activating the optical source.

11. Integrated plasmonic sensing device according to claim 1, wherein, when in use, a change in material composition within the nanocavity results in a change in efficiency of power transfer between the optical source and the detector; or, wherein, when in use, a geometric change in the nanocavity results in change in efficiency of power transfer between the optical source and the optical detector when an external stimulus is applied.

12. Integrated plasmonic sensing device according to claim 1, wherein a quantity of material that responds to an applied secondary stimulus is placed within the nanocavity to facilitate sensing of said secondary stimuli.

13. Integrated plasmonic sensing device according to claim 1, wherein when a quantity of material that absorbs power from the optical source and later transfers power to the detector is placed within the nanocavity.

14. Integrated plasmonic sensing device according to claim 1, wherein the thickness of said optical active layer is selected such that a single propagating guided plasmon mode is supported.

15. A plasmonic sensor pixel array, comprising a plurality of plasmonic pixel sensors, each plasmonic pixel sensor comprising at least part of an integrated plasmonic sensing device according to claim 1.

16. A plasmonic sensor pixel array according to claim 15 further comprising:
   one or more dielectric layers formed over at least part of said plasmonic pixel sensors, said one or more dielectric layers comprising one or more micro-channels in contact with at least part of nanocavities associated with said plasmonic pixels sensors, said micro-channels being configured to guide a fluid and/or gas into or through said nanocavities.

* * * * *